United States Patent [19]

Mitsch et al.

[11] 4,094,911

[45] June 13, 1978

[54] POLY(PERFLUOROALKYLENE OXIDE) DERIVATIVES

[75] Inventors: Ronald A. Mitsch, Little Canada; Joseph La Mar Zollinger, Maplewood, both of Minn.

[73] Assignee: Minnesota Mining and Manufacturing Company, Saint Paul, Minn.

[21] Appl. No.: 373,200

[22] Filed: Jun. 25, 1973

Related U.S. Application Data

[63] Continuation-in-part of Ser. No. 805,885, Mar. 10, 1969, abandoned, which is a continuation-in-part of Ser. No. 70,540, Sep. 8, 1970, Pat. No. 3,810,874.

[51] Int. Cl.$^2$ .............................................. C07C 43/30
[52] U.S. Cl. .............................. 260/615 A; 260/609 R; 260/46.5 R; 260/613 B; 548/305; 260/47 CP; 548/358; 562/87; 260/61; 562/180; 562/182; 260/65; 544/180; 260/75 H; 260/75 N; 260/75.5 R; 260/77.5 CH; 260/77.5 AP; 260/78 R; 260/78 TF; 260/78.41; 260/302 F; 260/307 D; 260/308 D; 260/326.5 R; 260/346.7; 260/348.11; 260/448.2 R; 260/448.2 B; 260/448.2 N; 260/448.8 R; 260/456 F; 260/465.6; 260/514 J; 260/534 E; 260/543 H; 260/561 R; 260/564; 260/559 R; 260/584 B; 260/590 D

[58] Field of Search .......... 260/302 F, 307 D, 308 D, 260/346.7, 348.11, 448.2 R, 448.2 B, 448.2 N, 448.8 R, 453 A, 456 F, 465.6, 514 J, 534 E, 543 H, 561 R, 554 R, 564, 584 B, 590 D, 594, 609, 613 B, 615 BF, 615 F, 615 A; 548/305, 358; 562/180, 182, 87; 544/180

[56] References Cited

U.S. PATENT DOCUMENTS

| 3,419,531 | 12/1968 | Trischler | 260/340 X |
|---|---|---|---|
| 3,419,532 | 12/1968 | Jackson | 260/77.5 |

OTHER PUBLICATIONS

Nasa SP-5901(01), Synthesis of Fluorinated Hydrocarbons, Mar. 4, 1968, pp. 14, 16.

*Primary Examiner*—Howard T. Mars
*Attorney, Agent, or Firm*—Cruzan Alexander; Donald M. Sell; William G. Ewert

[57] ABSTRACT

Polyfunctional poly(perfluoroalkylene oxide) compounds, such as compounds of the formula

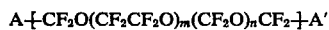

$$A\text{--}[CF_2O(CF_2CF_2O)_m(CF_2O)_nCF_2]\text{--}A'$$

where A and A' are reactive radicals containing a polymerizable functional group, e.g., hydroxyl, are provided, such compounds being useful as monomers in the preparation of polymeric materials, e.g., polyurethanes, possessing unusual low temperature stability and resistance to solvents.

11 Claims, No Drawings

POLY(PERFLUOROALKYLENE OXIDE) DERIVATIVES

RELATED APPLICATIONS

This application is a continuation-in-part of our copending applications Ser. No. 805,885, filed Mar. 10, 1979, now abandoned and Ser. No. 70,540, filed Sept. 8, 1970, now U.S. Pat. 3,810,874, the latter being a continuation-in-part of the former; these copending applications are relied on herein in their entirety and are incorporated herein by reference.

This invention relates to polyfunctional poly(perfluoroalkylene oxides) and their preparation.

BACKGROUND OF THE PRIOR ART

There are many applications, for example in the aerospace industry, in which sealants, gaskets, O-rings, solid propellant binders, etc., must have low temperature flexibility, high temperature stability, solvent resistance, and thermal and oxidative stability. Although recent prior art materials have been described which exhibit some of the above properties, there have not heretofore been provided polymers which satisfy the above requirements and additionally have satisfactory low temperature flexibility.

Polyurethanes have been prepared in the past by reacting hydroxyl-containing hydrocarbon polymers, such as poly(oxypropylene) triols, with aliphatic or aromatic diisocynates. Such prior art polyurethanes, though widely useful for many applications, do not have the low temperature flexibility, tensil and elongation, and the hydrolytic, thermal, and oxidative stability required for many other applications (such as solid propellant binders and other uses in the aerospace industry). Recently, fluorine-containing polyurethanes have been disclosed in the art which do have some thermal and oxidative stability, but they and their methods of preparation suffer from a number of disadvantages or limitations, as discussed below.

In *Vysokomolekulyarnye Soedineiya* Vol. (A) 9, No. 11, p. 2482 (1967) and *Jour. of Polymer Sci.* Part A-1, Vol. 5, p. 2757 (1967), non-rubbery fluorine-containing polyurethanes are disclosed as being prepared by either the reaction of chloroformate derivatives of hydroxy compounds with fluorine-containing diamines (which reaction evolves corrosive, bubble-forming hydrogen chloride) or the reaction of fluorine-containing hydroxy compounds (rather than prepolymers) with aliphatic diisocyanates. These polyurethanes have a high ratio of urethane groups to the total weight of the polymer, and consequently a low fluorine content. NASA Publication No. SP-5901(01), p. 14 (1968), published by NASA's Office of Technology Utilization, discloses fluorine-containing polyurethanes, having pendant —$CF_3$ groups in the backbone, prepared by reaction of an excess of aliphatic diisocyanate with hydroxyl-and fluorine-containing prepolymers having hydroxyl functionalities typically less than two, using undesirably high reaction temperatures. Though these prior art fluorine-containing polyurethanes do have some thermal and oxidative stability, they do not have very low temperature flexibility — a property which is highly desirable where such products are used, for example, as low temperature adhesives and propellant binders.

DESCRIPTION OF THE INVENTION

This invention provides novel polyfunctional-terminated poly(perfluoroalkylene oxides) which are very useful for the preparation of novel polymers which have unexpectedly low glass transition temperatures and are flexible at low temperature, and which possess solvent resistance with good hydrolytic, thermal, and oxidative stabilities.

In accordance with the invention, there are provided linear polyfunctional-terminated poly(perfluoroalkylene oxide) compounds of the formula

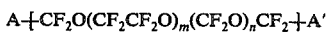

$$A + CF_2O(CF_2CF_2O)_m(CF_2O)_nCF_2 + A' \qquad I$$

where A and A' are reactive radicals, preferably organic, bonded to a terminal —$CF_2$—group (as shown) and containing a polymerizable group and $m$ and $n$ designate the number of randomly distributed perfluoroethyleneoxy and perfluoromethyleneoxy backbone repeating subunits, respectively, the ratio $m/n$ being 0.2/1 to 5/1, said compounds having a number average molecular weight, $\overline{M}_n$, in the range of 500 to 20,000 or higher, preferably 800 to 15,000. The compounds of this formula can be homopolymerized or copolymerized for the preparation of thermally stable, solvent resistant polymers such as polyurethanes, polyesters, polysiloxanes polyamides and others, as disclosed in our pending filed applications Ser. NO. 805,885 and Ser. No. 70,540 which are incorporated herein in their entirely by reference. The glass transition temperatures, $T_g$, of formula I compounds are in general lower than −78° C. and preferably lower than −100° C., and can be as low as −125° C. or even lower, e.g., −130° C. These advantageously low glass transition temperatures are also characteristic of the polymers prepared from said compounds and can be further lowered by increasing the oxygen/fluorine content in the compound or by increasing the length of the poly(perfluoroalkylene oxide) segment.

While the segment-terminating radicals are usually and preferably —$CF_2$—, segments containing —$C_2F_4$—, —$C_3F_6$— or similar perfluoroalkylene radicals can be prepared and have essentially the same properties as do the —$CF_2$— terminated segments.

The backbone of the compounds of formula I is terminated by perfluoromethylene groups bearing a polymerizable functional group linked to said perfluoromethylene groups by divalent radicals free of non-aromatic double bonds.

Preferably A and A' in the polyfunctional-terminated poly(perfluoroalkylene oxide) compound are —$X_aYZ_b$ or —$X'_{a'}$, $Y'Z'_{b'}$, respectively, where X and X' are each a polyvalent, preferably divalent, linking organic radical such as —CONR—, —$CO_2$—, —COS—, —CO—,

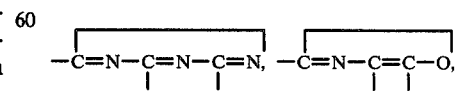
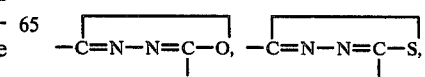

-continued

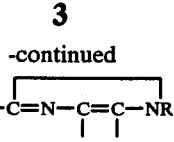

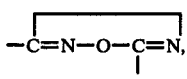

a and a' are zero or 1 (and can be the same or different), b and b' are integers of 1-3 (and can be the same or different). R is hydrogen, lower alkyl (e.g., $CH_3$, $-CH_2CF_3$, $-C_6H_{13}$), aryl of less than 13 carbon atoms (e.g., $-C_6H_5$, $-C_6H_4CH_3$, $C_{10}H_7$) or $-YZ_b$ radical. Y and Y' are polyvalent linking organic radicals free of olefinic unsaturation such as alkylene (e.g., $-CH_2-$, $-C_2H_4-$), oxa-alkylene (e.g., $-CH_2OCH_2-$), cycloalkylene (e.g. $-c-C_6H_{10}-$), thia-alkylene (e.g., $-CH_2SCH_2-$), and arylene (e.g. $-C_6H_4-$, $-C_6H_4OC_6H_4-$), or combinations thereof, such as aralkylene and alkarylene. Z and Z' are polymerizable functional groups which can vary such as $-OH$, $-SH$, $-SR'$, $-NR_2'$, $-CO_2H$, $-SiR_d'Q_{3-d}$, $-CN$, $-NCO$,

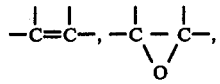

$-CO_2R'$, $-OSO_2CF_3$, $-OCOCl$, $-OCN$, $-N(R')CN$, $-(O)COC(O)-$, $-N=C$, $-I$, $-CHO$, $-CH(OCH_3)_2$, $-SO_2Cl$, $-C(OCH_3)=NH$, $-C(NH_2)=NH$, and

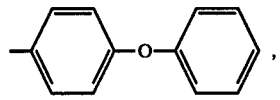

wherein R' is hydrogen, aryl, or lower alkyl, Q is halogen, $-OR'$, $-OCOR'$, or $-CH=CH_2$; and d is zero or an integer of 1 to 3. Z and Z' may also be $-OCR_1R_2R_f$ or

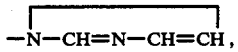

wherein $R_1$ is hydrogen, lower alkyl or lower fluoroalkyl, $R_2$ is hydrogen or lower alkyl and $R_f$ is lower fluoroalkyl. The polymerizable functional group in A and A' is one which will undergo electrophilic, nucleophilic, or free radical reaction to form a polymeric product.

Thus, the linear functional-terminaled poly(perfluoroalkylene oxide) compounds of formula I can be polymerized or copolymerized to form polymers comprising recurrent backbone units of the formula $$-CF_2O(CF_2CF_2O)_m(CF_2O)_nCF_2- \qquad II$$

(This formula occasionally abbreviated hereinafter as $-R_{fo}-$). and organic linking radicals, where m and n designate the number of randomly distributed perfluoroethyleneoxy and perfluoromethyleneoxy backbone repeating subunits, respectively, the ratio m/n being 0.2/1 to 5/1, preferably 0.5/1 to 2/1, wherein said recurrent backbone units are joined by said organic linking radicals attached through a carbon, oxygen, sulfur or nitrogen atom thereof contained in a chain of not fewer than 3 atoms. Typically, the polymers have a molecular weight of at least 1100, preferably at least 5000, and frequently as high as 2,000,000 or more.

The linear polyfunctional-terminated poly)perfluoroalkylene oxide) compounds of formula I are conveniently prepared, for example, from the ester, carboxy, or acyl halide-terminated precursors which are shown and described along with their preparation in Italian Patent No. 817,809, incorporated herein by reference.

The linear hydroxy-terminaed poly(perfluoroalkylene oxide) reactants or prepolymers used in this invention are preferably those of the general formula:

$$R-CF_2O-(CF_2CF_2O)_m(CF_2O)_n-CF_2-R' \qquad III$$

where R and R' are hydroxy-substituted organic radicals, such as hydroxy-substituted aliphatic or hydroxy-substituted aromatic radicals, or R and R' are preferably methylol, $-CH_2OH$, or $-C(O)N(R'')CH_2CH_2OH$ (where R" is hydrogen, lower alkyl, e.g. methyl, or ethylol, $-CH_2CH_2OH$), and m and n designate randomly distributed perfluoroethyleneoxy and perfluoromethyleneoxy backbone units, the ratio m/n being 0.2/1 to 5/1, preferably 0.5/1 to 3/1 and typically 0.7/1 to 1.6/1. The number average molecular weight, $\overline{M}_n$, is in the range of 500 to 10,000, preferably 800 to 5000. The glass transition temperatures, $T_g$, of these prepolymers, as well as the polyurethanes prepared therefrom, are much lower than any known fluorine-containing polymers, and in general are lower than $-78°$ C. and preferably lower than $-90°$ C., and can be as low as $-125°$ C.; the higher the oxygen-to-fluorine content in the prepolymer, the lower the glass transition temperature. (The "glass transition temperature" of a polymer is that temperature above which a polymer is soft or rubbery, that is, flexible, and blow which it is a hard and brittle glass; such temperature is generally determined by differential thermal analysis, "DTA", or changes in coefficient of expansion.) The propolymers are generally clear, colorless liquids at room temperature, with low bulk viscosity (e.g., 125 cps at 27° C.), properties which are advantageous in using these materials.

Generally, the hydroxy-terminated prepolymer will be a mixture of such compounds having a different backbone or chain lengths. Representative prepolymers useful in this invention to form polyurethanes, and coming within the scope of general Formula III above, are the following:

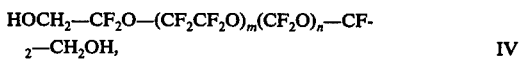    IV

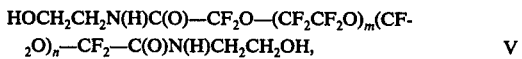    V

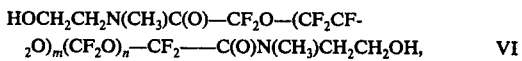    VI

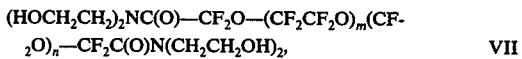    VII and mixtures thereof. Others are described hereafter, e.g., Examples XIII, XX.

The simplest methylol-terminated poly(perfluoroalkylene oxide) propolymers, illustrated by Formula IV above, are the preferred prepolymers to be used in preparing the polyurethanes of this invention because of the greater low temperature flexibility and hydrolytic stability of the polyurethanes prepared therefrom.

The novel methylol-terminated poly(perfluoroalkylene oxides) of this invention can be prepared by reduction of their ester-terminated precursors, such as the lower alkyl esters, e.g.,

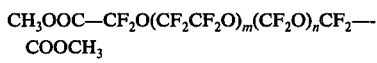

$$CH_3OOC{-}CF_2O(CF_2CF_2O)_m(CF_2O)_nCF_2{-}COOCH_3 \qquad \text{VIII}$$

where $m$ and $n$, and the ratio $m/n$, are as defined above for Formula II. Such esters can be reduced to the methylol prepolymers by various reduction procedures, such as catalytic hydrogenation in the presence of a copper chromium oxide catalyst (see U.S. Pat. Nos. 2,911,444 and 3,314,987), but preferably they are reduced in the presence of a complex metal hydride, such as lithium aluminum hydride, $LiAl_4$, or an alkali metal borohydride, such as sodium borohydride, $NaBH_4$, the reduction being carried out in an inert solvent such as tetrahydrofuran, diglyme, or dioxane, and at reflux temperatures. Generally the reaction product will be a mixture of methylol-terminated poly(perfluoroalkylene oxides) of different chain length. If desired, such a mixture can be fractionated, e.g., by distillation, chromatography, selective extraction, and other techniques, to obtain individual fractions of more limited molecular weight distribution.

Instead of reducing the ester-terminated precursors, the corresponding carboxy- or acyl halide-terminated precursors can be reduced, preferably with $LiAlH_4$, to form the methylolterminated propolymers. The ethylol-substituted amide-terminated prepolymers illustrated by Formulas V, VI and VII above can be readily prepared by reacting said diester precursors, VIII, or said acyl halide precursors, with a corresponding ethanol amine, i.e., $HOCH_2CH_2NH_2$, $HOCH_2CH_2NHCH_3$, and $(HOCH_2CH_2)_2NH$, respectively.

The diester precursors, VIII, themselves, and the other precursors mentioned above, and their preparation are disclosed in Italian Pat. No. 817,809 (e.g., Example 11 thereof).

Where the prepolymers have terminal hydroxy-substituted aliphatic groups other than methylol (i.e., prepolymers other than those like Formulas IV to VII ), they can be prepared, for example, by reacting said ester- or acyl halide-terminated precursors with higher aliphatic amino alcohols, such as propanol amine or ω-aminoundecyl alcohol. The hydroxy-substituted aromatic-terminated prepolymers can be prepared, for example, by reacting said acyl halide-terminated precursors with aminophenols, such as m-aminophenol, hydroxyalkyl-substituted aromatic amines, such as hydroxyethylaniline, or hydroxyalkyl-substituted aralkyl amines, such as 1-methyl-1-hydroxymethylbenzylamine. Said acyl halide- or ester-terminated precursors can be converted to other hydroxy-substituted aliphatic or aromatic prepolymers with methylene or substituted methylene linkages between the polymer backbone and the hydroxy-substituted terminal groups. For example, by reacting the acyl halide-terminated precursor with potassium iodide to produce an iodide-terminated intermediate, then reacting the latter with ethylene to produce an iodoethylene- or iodopolyethylene-terminated intermediate, and then saponifying the latter. As another example, said acyyl halide- or ester-terminated precursors can be reacted with organometallic compounds, such as ethyl magnesium bromide or mixed methyl and isopropyl magnesium bromides, to produce prepolymers with terminal groups that characterize the propolymers as tert- or sec-alcohois. As another example, the acyl halide- or ester-terminated precursors can be reacted with excess polyols, such as neopentylglycol, to produce 3-hydroxy-2,2-dimethyl propyl ester terminal groups. The methylol-terminated propolymers of Formula IV can be converted to other hydroxy-substituted aliphatic or armoatic terminated prepolymers with ester or ether linkages in the terminal groups. For example, reaction of the methanlol-terminated prepolymer with cyclic esters, such as beta-propiolactone to produce hydrocypropionates; or by reaction with ethylene oxide and/or 1,2-propylene oxide to produce oxyalkylene or polyoxyalkylene diols.

In the event such hydroxy-substituted aliphtic- or aromatic-terminated prepolymers are used rather than the methylol-terminated prepolymers (of Formulas IV to VII), the aliphatic or aromatic portions of such terminal groups should preferably be less than 15 to 20 weight percent of the prepolymer, and usually contain less than about 12 carbon atoms, in order to retain the desired thermal stability, low temperature flexibility, and other properties imparted to the prepolymers by the perfluoroalkylene ether backbone. Said aliphatic and aromatic portions of said terminal groups should not contain any active hydrogen atoms more reactive with the isocyanato groups of the polyisocyanates than the hydroxy substituent; however, said aliphatic and aromatic portions can contain other substituents which are non-reactive with said isocyanato group.

Hydroxy-terminated poly(perfluoroalkylene oxides) having more than two terminal hydroxy groups can be prepared, for example, by reacting the dimethylol-terminated compound with up to two molar equivalents of 2,3-epoxy-1-propanol in the presence of a basic catalyst. Such polyhydroxy derivatives are useful as compatible cross-linking components in the preparation of urethane polymers.

Other compounds of Formula I are prepared from the acid, ester, or acyl halide-terminated poly(perfluoroalkylene oxides) by known reactions as indicated in Table I.

Table I

| A and A' of Formula I | Reactant |
|---|---|
| 1. $-CONHCH_2-CH{=}CH_2$ | $H_2NCH_2-CH{=}CH_2$ |
| 2. $-CONH(CH_2)_3CO_2H$ | $H_2N(CH_2)_3CO_2H$ |
| 3. $-CON(CH_3)CH_2CH_2OH$ | $HN(CH_3)CH_2CH_2OH$ |
| 4. $-CONHCH_2CH_2NH_2$ | $H_2NCH_2CH_2NH_2$ |
| 5. $-CONHCH_2CH_2SH$ | $H_2NCH_2CH_2SH$ |
| 6. $-CONH(CH_2)_3Si(OCH_3)_3$ | $H_2N(CH_2)_3Si(OCH_3)_3$ |

Table I-continued

| A and A' of Formula I | Reactant |
|---|---|
| 7. —CONH—(3-hydroxyphenyl) | 3-aminophenol (H₂N—C₆H₄—OH) |
| 8. —CONH—C₆H₄—CH₂CO₂H (para) | H₂N—C₆H₄—CH₂CO₂H |
| 9. —CONH—(2,5-dihydroxyphenyl) | 2-amino-1,4-dihydroquinone (H₂N—C₆H₃(OH)₂) |
| 10. —CONH—C₆H₄—Si(CH₃)₂OC₂H₅ | H₂N—C₆H₄—Si(CH₃)₂OC₂H₅ |
| 11. —CONH—C₆H₄—CH₂CH=CH₂ | H₂N—C₆H₄—CH₂CH=CH₂ |
| 12. —CONH—(3-isocyanato-4-methylphenyl) | OCN—(3-isocyanato-4-methylphenyl) |
| 13. —CONH—C₆H₄—O—C₆H₄—NCO | OCN—C₆H₄—O—C₆H₄—NCO |
| 14. —CONH—(cyclohexyl)—CH₂—(cyclohexyl)—NCO | OCN—(cyclohexyl)—CH₂—(cyclohexyl)—NCO |
| 15. benzoxazol-5-ol (—C= attached) | 1) H₂N—(2,4-dihydroxyphenyl); 2) Heat |
| 16. 5-(3,4-diaminophenyl)-1H-benzimidazol-2-yl (—C=) | 1) H₂N—C₆H₃(NH₂)—C₆H₃(NH₂)(NH₂); 2) Heat |
| 17. 2-benzothiazolyl-6-carboxylic acid (—C=) | 1) H₂N—C₆H₃(SH)—CO₂H; 2) Heat |
| 18. 2-(1,3,4-oxadiazol-2-yl)propyl: —C=N—N=C(—C(CH₃)=CH₂)—O— | 1) H₂NNHCOC(CH₃)=CH₂; 2) Dehydration |
| 19. —CO₂CH₂C(CH₃)₂CH₂OH | HOCH₂C(CH₃)₂CH₂OH |
| 20. —CO₂CH₂CH(OH)CH₃ | CH₃CH—CH₂ (epoxide, O) |
| 21. —CO₂CH₂CH=CH₂ | CH₂=CHCH₂OH |
| 22. —CN | 1) NH₃; 2) Dehydration |

Table I-continued

| A and A' of Formula I | Reactant |
|---|---|
| 23. (triazine ring with CH=CH₂, CF₃ substituents) | 1) NH₃<br>2) Dehydration<br>3) H₂N—C(=NH)—CF₃<br>4) (CH₂=CHCO)₂O |
| 24. —CH₂OH | LiAlH₄ |
| 25. —CH₂OCH₂CH(OH)CH₂OH | Compound 24 + CH₂—CHCH₂OH (epoxide) |
| 26. —CH₂O)CH₂CH—CH₂ (epoxide) | Compound 24 + CH₂—CHCH₂Br (epoxide) |
| 27. —CH₂OCH₂CH=CH₂ | Compound 24 + CH₂=CHCH₂Br |
| 28. —CH₂OCO—(C₆H₄)—NH₂ | Compound 24 + (anthranilic anhydride / isatoic anhydride) |
| 29. —CH₂OSO₂CF₃ | Compound 24 + CF₃SO₂F + (C₂H₅)₃N |
| 30. —CH₂OCN | Compound 24 + NCCl + (C₂H₅)₃N |
| 31. —CH₂O—(C₆H₄)—NH₂ | 1. Compound 29 + NaO—(C₆H₄)—NO₂<br>2. H₂ |
| 32. —CH₂O—(C₆H₄)—NCO | Compound 31 + COCl₂ |
| 33. —CH₂O—(phthalic anhydride) | 1) Compound 29 + NaO—(C₆H₄)(CO₂CH₃)₂<br>2) Hydrolysis<br>3) (CH₃CO)₂O |
| 34. —CH₂—(C₆H₄)—O—(C₆H₄)—OCN | 1) Compound 29 + NaO—(C₆H₄)—O—(C₆H₄)—OH<br>2) ClCN + (C₂H₅)₃N |
| 35. —CH₂NH₂ | Compound 29 + NH₃ |
| 36. —CH₂NCO | Compound 35 + COCl₂ |
| 37. —CH₂NHCH₃ | Compound 29 + CH₃NH₂ |
| 38. —CH₂N(norbornene dicarboximide) | Compound 35 + (norbornene dicarboxylic anhydride) |
| 39. —CH₂N(norbornane dicarboximide with Si(CH₃)₂OCOCH₃) | Compound 38 + HSi(CH₃)₂OCOCH₃ + H₂PtCl₆ |
| 40. —CH₂OCOC(CH₃)=CH₂ | Compound 24 + CH₂=C(CH₃)COCl |
| 41. —CH₂I | Compound 29 + NaI |
| 42. —CH₂SH | 1) Compound 29 + CH₃COSNa<br>2) Hydrolysis |

Table I-continued

| | A and A' of Formula I | Reactant |
|---|---|---|
| 43. | $-CH_2\overset{\oplus}{N}\equiv\overset{\ominus}{C}$ | 1) Compound 35 + $HCO_2CH_3$<br>2) $COCl_2$ + $(C_2H_5)_3N$ |
| 44. | $-NCO$ | 1) $NaN_3$<br>2) Heat |
| 45. | $-COC_6H_5$ | $Cd(C_6H_5)_2$ |
| 46. | $-C(CH_3)_2OH$ | 1) $CH_3MgBr$<br>2) $H^+$ |
| 47. | $-CHO$ | $LiAlH_4$ |
| 48. | $-C(CH_3)=CH_2$ | Compound 46 + $P_2O_5$ |
| 49. | $-CH_2N(CN)CH_3$ | Compound 37 + ClCN + $(C_2H_5)_3N$ |
| 50. | $-I$ | 1) $Ag_2O$<br>2) $I_2$ |
| 51. | $-CH=CH_2$ | Compound 47 + $CH_2=P(C_6H_5)_3$ |
| 52. | $-C(OCH_3)=NH$ | Compound 22 + $CH_3OH$ + $(C_2H_5)_3N$ |
| 53. | $-CH_2-SO_2Cl$ | Compound 42 + $Cl_2$ + $H_2O$ |
| 54. | $-CH(OCH_3)_2$ | Compound 47 + $CH_3OH$ + acid |
| 55. | $-C(NH_2)=NH$ | Compound 22 + $NH_3$ |
| 56. | 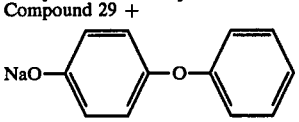 | Compound 29 + 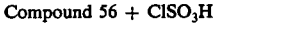 |
| 57. | 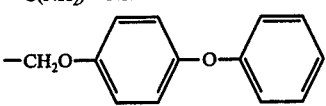 | Compound 56 + $ClSO_3H$ |
| 58. | 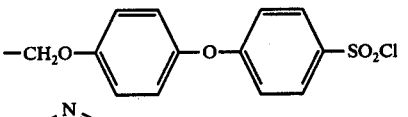 | Compound 22 + $HN_3$ |

Compounds 1 to 6, inclusive, of Table I, aliphatic amides, can generally be prepared by reaction of a parent methyl ester $$CH_3O_2CCF_2O(CF_2CF_2O)_m(CF_2O)_nCF_2CO_2CH_3 \qquad IX$$

with an amino-substituted compound, as specifically illustrated in Example I hereinafter.

Further description of the preparations of said functionally-terminated poly(perfluoroalkylene oxides) will be omitted in the interest of brevity since in most cases they follow classical methods, such as described in "Organic Functional Group Preparations", by Sandler & Karo, Academic Press, Inc., N.Y. N.Y. (1968).

The functionally-terminated poly(perfluoroalkylene oxides) of this invention, in addition to their utility as prepolymers for the preparation of polymers, are also useful as lubricants, viscosity index additives for perhalogenated lubricants, hydraulic fluids, water and oil repellants, surface active agents, anti-corrosion agents, anti-stick or release agents of molds, flotation agents, and plasticizers for fluorinated plastics. Objects and advantages of this invention are furthere illustrated by the following examples.

EXAMPLE I

In this example, an ethylol-substituted, amide-terminated prepolymer was prepared by slowly adding and stirring 0.9 g. of ethanolamine to 10.2 g. of a methyl diester precursor of formula IX ($\overline{M}_n$ = 1400 and $m/n$ = 1.55). After stirring the mixture for 1 hr., infrared analysis indicated complete conversion of the diester precursor to the amide-terminated prepolymer. The reaction mixture was dissolved in 125 ml. diethyl ether, washed with 3–10 ml. portions of water, and dried over calcium sulfate. Removal of the calcium sulfate and ether yielded 9.5 g. of the pale yellow prepolymer, having the structure $$HOCH_2CH_2NHC(O)CF_2O(CF_2CF_2O)_m(CF_2O)_nCF_2CONHCH_2CH_2OH \qquad X$$

confirmed by its infrared spectrum, useful in making polyurethane.

EXAMPLE II

Compounds 7 to 11, inclusive, of Table I, aromatic amides, can be prepared by reaction of an activated ester with an aromatic amine, as specifically illustrated in this example.

To a mixture of 200 g. (0.38 mole) of the dimethylester of formula IX ($\overline{M}_n$, 2100; $m/n$, 0.6) and 200 g. (0.86 mole) of 1,1,5-trihydrooctafluoropentyl alcohol in a 500 ml. glass flask was added 10 drops of sulfuric acid (conc.) and 1.5 ml. of trifluoromethanesulfonic anhydride as transesterification catalysts. The mixture was refluxed for 10 days with 0.5 additional anhydride catalyst being added on the first, second, third and sixth days. Five ml. of distillate was removed through a 30 cm. Vigreux columm on the seventh and eight days. Part of the fluorinated pentyl alcohol was removed by distillation. The lower liquid layer of the pot residue was heated (140° C.) at aspirator pressure, then cooled, dissolved in 1,1,2-trichlorotrifluoroethane, treated with activated charcoal, filtered, and the solvents removed under reduced pressure with final heating at full oil pump vacuum for 16 hrs. on the steam bath. The colorless liquid ester product weighed 183 g. The carbonyl peak for the ester end group, $CO_2CH_2(CF_2)_4H$, is at 5.49 microns, consistent with a product of structure XI:

H(CF₂)₄CH₂O₂CCF₂O(CF₂CF₂O)ₘ(CF₂O)ₙCF₂CO₂CH₂(CF₂)₄H    XI

Proton nuclear magnetic resonance analysis showed peaks ar 4.03τ (triple triplet) and 5.22 (triplet) consistent for —CF₂H and —CH₂CF₂, respectively.

To a 100 ml. glass flask fitted with reflux condenser and drying tube was placed 22.0 g. (0.01 mole) of the diester of formula XI and 6.0 g. of 4-amino-4'-hydroxydiphenyl ether. After refluxing overnight and removal of solvent, the residual product was dissolved in diethyl ether and extracted with 0.2 N-hydrochloric acid and water. After drying over calcium sulfate, filtration and removal of solvent 16.5 g. of a pale orange crystalline solid, m.p. 110°-113° C., was obtained. This amido phenol is soluble in diethyl ether acetone and acetonitrile at room temperature. It is insolubale in 1,1,2-trichlorotrifluoroethane and chloroform. Proton nmr and infrated spectra support the proposed structure, formula XII. Infrared peaks are at 3.04 and 5.84 microns for NH, OH and C=O, respectively.

HOC₆H₄OC₆H₄NHCOCF₂O(CF₂CF₂O)ₘ(CF₂O)ₙCF₂CONHC₆H₄OC₆H₄OH    XII

EXAMPLE III

Amides free of isocyanate-reactive hydrogen atoms, such as comppounds 12 to 14, inclusive, of Table I can conveniently be prepared from dicarboxylic polyethers:

HO₂CCF₂O(CF₂CF₂O)ₘ(CF₂O)ₙCF₂CO₂H    XIII in accordance with this example.

To a refluxing solution of 90 g. of toluene -2,4-diisocyanate in 150 ml. of xylene hexafluoride in a 500 ml. glass flask was added, over a two-hour period, 50 g. of a dicarboxylic acid of formula XIII ($\overline{M_n}$ = 2700, m/m = 0.6) in 25 ml. of xylene hexafluoride. Refluxing was continued for two days to complete the reaction and to eliminate carbon dioxide. Most of the solvent was removed by distillation and the cooled reaction mixture washed four times with petroleum ether. The pure isocyanate-amide end-capped liquid polymer (42 g.) was isolated by pumping under good vacuum at room temperature.

Infrared absorptions at 3.05 and 6.5 microns for NH, 4.40 microns for NCO, and 5.87 microns for C=O, are consistent with the structure:

OCNC₆H₃(CH₃)NHC(O)CF₂O(CF₂CF₂O)ₘ(CF₂O)ₙCF₂CONHC₆H₃(CH₃)NCO    XIV

-Polycarbodiimides can be prepared from isocyanate terminated poly(perfluoroalkylene oxides) by condensation in the presence of 1-phenyl-3-methyl-3-phospholene oxide as catalyst at 25°-100° C. Polyisocyanurates can also be made.

EXAMPLE IV

A useful class of poly(perfluoroalkylene oxides) is those terminated by 5-membered heterocyclic rings including the radical

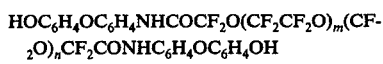

wherein G represents an atom of oxygen, nitrogen, or sulfur. Certain of theses, such as compounds 15, 16, and 17 of Table I, which contain the structure:

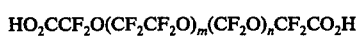

can be prepared by dehydration of the corresponding ortho-substituted carboxanilide, as more specifically illustrated in this example.

To a 100 ml. glass flask was added 10.6 g. of

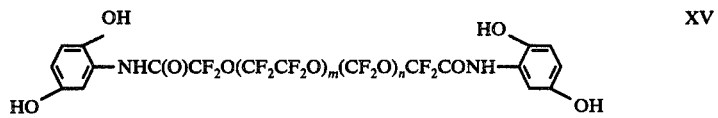

prepared as in Example II. The flask was heated at 165°-175° C. in an oil bath at water aspirator vacuum for a total of 5.5 hrs. to yield 10.2 g. of a dark green oil. Treatment of 1,1,2-trichlorotrifluoroethane solution with decolorizing charcoal gave 7.8 g. of an amber oil. Infrated analysis showed peaks characteristic of a benzoxazole besides a small absorption of 3.0 microns due to hydroxyl. Fluorine nuclear magnetic resonance (nmr) peaks are at 69.0 and 70.9 φ for terminal CF₂ groups. $\overline{M_n}$ was 2100 as measured by vapor phase osmometry in 1,1,2-trichlorotrifluoroethane. The data are consistent with the structure.

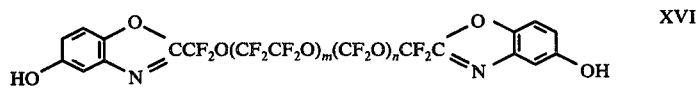

By reactions of acyl hydrazides, such as monomethacrylyl hydrazide, with the diester of formula IX, as shown in Example I, and dehydrating the resulting amide-terminated poly(perfluoroalkylene oxide) in accordance with this example, compounds such as the following can be prepared:

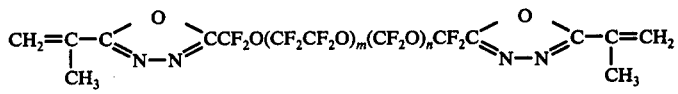

XVII

Polymerizable ester-terminated poly(perfluoroalkylene oxides) such as compound 20 of Table I, can be prepared by reaction of an alkylene oxide, such as propylene oxide, with the diacid of formula XIII. By using an excess of the alkylene oxide, polyether terminated compounds useful as surfactants in organic solvents can be prepared.

Polymerizable ester-terminated compounds such as compounds 19 and 21 of Table I, can conveniently be prepared by transesterification from the diester of formula XIII, using mercury salts as catalysts.

EXAMPLE V

Nitrile-terminated poly(perfluoroalkylene oxides) such as compound 22 of Table I, are useful, for example, in the preparation of triazine polymers, the preparation of which is illustrated below.

In a 500 ml. round-bottom glass flask was placed 22.8 g. (0.016 mole) of the liquid dicarbonamide $$H_2NC(O)CH_2O(CF_2CF_O)_m(CF_2O)_nCF_2CONH_2 \quad \text{XVIII}$$

($\overline{M}_n = 1400$, $m/n \approx 1.55$), 140 g. of sand, and 57 g. (0.40 mole) of $P_2O_5$. The mixture was shaken vigorously until it became nearly free-flowing, then heated in a sand bath and under a vacuum of 50 mm. of mercury. The nitrile product began distilling (through a short path distilling head) when the pot temperature reached 195° C. The pressure was reduced to 20 mm. at a pot temperature of 227° C. and to 2.5 mm. at a pot temperature of 248° C. Total heating time was about 3 hrs. The yield of colorless liquid was 19.2 g., $n_D 24 = 1.2894$. Infrared absorption of the group —CH is 4.39 microns. Fluorine nuclear magnetic resonance peaks for terminal $CF_2$ groups are 58.6 and 60.0 $\phi^*$.

The data are consistent with the structure

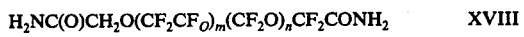

NCCF$_2$O(CF$_2$CF$_2$O)$_m$(CF$_2$O)$_n$CF$_2$CN   XIX

EXAMPLE VI

Hydroxy-terminated poly(perfluoroalkylene oxides) such as compounds 24 and 25 of Table I, can be prepared, for example, by reduction of the diester of formula IX, as illustrated in this example.

Powdered lithium aluminum hydride (1.9 g., 0.05 mole) was added to 120 ml. of dry diethyl ether in a 500 ml., three-necked flask fitted with a mechanical stirrer, a reflux condenser fitted with a calcium sulfate drying tube, and gas-inlet tube, and the mixture stirred 4 hrs. under dry nitrogen. Fifty ml. of an ether solution of the methyl diester of Formula IX ($\overline{M}_n = 1800$ and $m/n = 1.4/1$) was added to the stirred solution of lithium aluminum hydride at a rate sufficient to maintain a gentle reflux. After all the ester had been added, the resulting mixture was heated at reflux overnight. Anhydrous methyl alcohol (20 ml.) was added to decompose the excess hydride, followed by addition of dilute sulfuric acid (37 g. of 36N $H_2SO_4$ in 100 ml. of water). The aqueous and organic layers were separated and the aqueous layer extracted 4 times with diethyl ether, and the resulting ether fractions and the organic layer combined and dried over calcium sulfate. The calcium sulfate and ether were removed from the combined ether fractions yielding 32.5 g. of water-white, liquid methylol-terminated poly(perfluoroalkylene oxide),

HOCH$_2$—CF$_2$O(CF$_2$CF$_2$O)$_m$(CF$_2$O)$_n$CF$_2$—CH$_2$OH   XX which was found to have a $\overline{M}_n$ of about 1800, a hydroxyl equivalent weight of 975 ± 50 and $T_g$ of −107° C. This methylol compound was useful in preparing polyurethane.

EXAMPLE VII

In this example, another methylol-terminated poly(perfluoroalkylene oxide) was prepared following the procedure of Example VI, using a similar methyl diester precursor ($\overline{M}_n$ of 3000, $m/n = 1.25/1$) except that Freon 113 trichlorotrifluoroethane was used for extraction instead of diethyl ether. The preparation yielded 40 g. of water-white, liquid methylol-terminated fluoro polymer, HOCH$_2$—CF$_2$O—(CF$_2$CF$_2$O)$_m$(CF$_2$O)$_n$—CF$_2$—CH$_2$OH, which was found to have a $\overline{M}_n$ of about 3000, and hydroxyl equivalent weight of 1550 ± 50.

EXAMPLE VIII

An ethylol-substituted, amide-terminated prepolymer was prepared by mixing 4.2 g. of the same ester precursor used in Example I with 0.47 g. of 2-(methyl amino)ethanol. The resulting product was dissolved in 50 ml. diethyl ether, washed with two 15 ml. portions of 5% aqueous hydrochloric acid, followed by washing with three 10 ml. portions of water, dried over calcuim sulfate. Removal of the calcium sulfate and ether yielded 4 g. of pale yellow prepolymer having the structure shown in Formula VI above.

EXAMPLE IX

A methyl diester precursor (see Formula VIII), $\overline{M}_n = 1940$, $m/n − 0.7/1$, was fractionated by precipitation and the molecular weight distribution of each fraction determined by vapor phase osmometry. Results are shown below.

TABLE II

| Fraction | $\overline{M}_n$ | Wt. % |
| --- | --- | --- |
| 1 | 1090 | 12 |
| 2 | 1800 | 17 |
| 3 | 2000 | 7 |
| 4 | 2350 | 10 |
| 5 | 2850 | 15 |
| 6 | 3000 | 14 |
| 7 | 3350 | 8 |
| 8 | 3750 | 8 |
| 9 | 4650 | 6 |
| 10 | 7830 | 2 |
| 11 | >7830 | 1 |

The above diester ($\overline{M}_n = 1940$) was reduced, following the procedure of Example VII, to the corresponding methylol-terminated prepolymer derivative, useful in preparing polyurethane.

EXAMPLE X

One gram of a methylol-terminated prepolymer ($\overline{M}_n = 1700$, $m/n − 0.7$), having the structure shown by Formula IV above and useful in preparing a polyurethane, was prepared by reduction of the corresponding methyl diester using the procedure of Example VI.

EXAMPLE XI

A 250 ml. flask was charged with 100 ml. of anhydrous ethyl ether and 12.74 g. of the methyl diester precursor used in Example VII. The mixture was cooled with an ice bath to about 5° C. and stirred. To the stirred solution, 0.38 g. of diethanolamine was slowly added, followed by adding 1.21 g. of 2-aminoethanol. The resulting mixture was warmed to room temperature and mixing continued for 2 hrs. The solution was then washed 4 times with 25 ml. portions of water, dried over calcium sulfate, filtered, and the ether solvent stripped off. The resulting mixed amide-terminated prepolymer amounted to 12.8 g. and was a pale yellow liquid; it was useful in preparing a polyurethane.

EXAMPLE XII

Twenty grams of the same methylol-terminated prepolymer used in Example X was dissolved in 20 ml. of Freon 113 trichlorofluoroethane, and the resulting solution poured into 200 ml. of methanol while stirring vigorously. The prepolymer fraction which settled out was removed and stripped at reduced pressure, yielding 13 g. of prepolymer fraction, $\overline{M}_n = 2840$, which was useful in making polyurethane.

EXAMPLE XIII

Another type of hydroxy-terminated poly(perfluoroalkylene oxide), containing more than one hydroxyl group on each terminating radical, was prepared as shown in this example.

To a 500 ml. round bottom glass flask was charged 105 g. of a formula XX compound ($\overline{M}_n = 2000$, $m/n - 0.6$). The system was degassed and blanketed with $N_2$, then 5.25 ml. of a $NaOCH_3$ solution in methanol (4.85 meq/g) was added through a syringe with magnetic stirring. Methanol was removed under reduced pressure while the mixture was heated to 65° C. The system was again blanketed with $N_2$, cooled to 45° C., and 1.85 g. of glycidol was added. After the mixture was stirred at 90° C. for 1½ hours, it was cooled, diluted with 150 ml. $CF_2ClCFCl_2$ and washed with 10 ml. of 10% aqueous $H_2SO_4$. The solution was dried, filtered and concentrated. After a final heating to 95° C. at 0.8 mm Hg the product was filtered through a sintered glass funnel to remove trace contaminants. A yellow clear product was obtained (98.5 g., 92.5%), a 50% solution of $$HOCH_2CF_2O(CF_2CF_2O)_m(CF_2O)_nCF_2CH_2OCH_2CH(OH)CH_2OH \qquad XXI$$

in unreacted formula XX diol. By using a 2:1 mol ratio of glycidol to formula XX diol instead of the 1:0.5 illustrated above, a completely di-substituted product was obtained. The product is useful as a crosslinking agent for urethane or polyester polymers.

EXAMPLE XIV

This example illustrates the preparation of an epoxy-terminated poly(perfluoroalkylene oxide).

To a 100 ml. glass flask was added 10 g. (0.0055 mol) of a dicarbinol of formula XX ($\overline{M}_n = 1800$), 25 ml. of 1,1,2-trichlorotrifluoroethane, 15 ml. of 1,2-dimethoxyethane, and 0.64 g. (0.013 mol) of sodium hydride (50% in mineral oil). The mixture was refluxed for one hour. To this refluxing gelatinous mixture was added over a 5-minute period 2.4 g. of 1-bromo-2,3-epoxypropane in 5 ml. 1,2-dimethoxyethane. The mixture began to clear and a solid began building up on the flask walls during the 2 hours reflux time. The cooled clear solution was decanted from solids, washed three times with water, and concentrated under vacuum to yield 5 g. (about 50% yield) of pale yellow liquid, $n_D^{24} = 1.3133$. Proton nuclear magnetic resonance absorption peaks are as follows: 8.2τ, 6.4τ, 7.0τ, 7.4τ. These data are consistent with the structure:

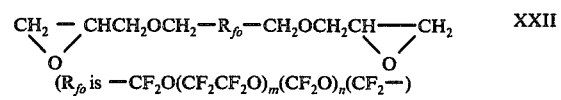

The dipoxide was polymerized to a solvent resistant elastomer useful for low-temperature gaskets by heating with 1–5% triethylenediamine or $(CF_3SO_3)_2Zn$ at about 100° C. for eight hours. Heating the diepoxide with an equimolar amount of formula XXVII diamine and 5% tris-dimethylaminomethylphenol for 16 hours at 140° C. produced crosslinked elastomer suitable as a cryogenic sealing material.

EXAMPLE XV

This example illustrates the preparation of an amino-ester-terminated poly(perfluoroalkylene oxide).

In a dry 500 ml. flask was placed 50 g. of formula XX dicarbinol ($\overline{M}_n$ about 2000), 11 g. of isatoic anhydride (m.p. 240°–242° C.), recrystallized from ethanol, 250 ml of redistilled benzotrifluoride, 10 ml of dry dimethylsulfoxide and 0.5 ml triethylamine catalyst. The mixture was refluxed (water condenser connected through a bubbler and drying tube) for 15.5 hrs. There was some foaming initially due to carbon dioxide evolution, but gas evolution slowed as the reaction proceeded. The pale yellow homogeneous reaction mixture was concentrated under water aspirator vacuum. 1,1,2-trichlorotrifluoroethane (300 ml.) was added to the liquid residue and then the mixture filtered to separate excess isatoic anhydride. The filtrate was washed with two 100 ml. portions of water, treated with sodium sulfate, filtered and concentrated under vacuum and finally filtered under vacuum through a fine porosity sintered glass funnel to yield 51.5 g. (92%) of a pale yellow, clear liquid. Infrared bands are 2.86 and 2.94 microns for $NH_2$ and 5.85 microns for C=O of the ester function. Proton nuclear magnetic resonance peaks are as expected: 2–3.6τ complex for aromatic hydrogen, 4.58τ (broad) due to $NH_2$, and 5.40τ (triplet) for methylene in —$OCF_2CH_2O$—.

These properties are consistent with the structure:

EXAMPLE XVI

This example illustrates the preparation of a diester suitable for formation of polymers by reaction with, for example, diamino or dihydroxy compounds, as well as an intermediate for formation of other difunctionally substituted poly(perfluoroalkylene oxides).

A mixture consisting of 38.9 grams of 2000 molecular weight alpha, omega-dihydroxy perfluoroether polymer of formula XIV ($m/n$ of 0.6) ml. $CF_2ClCFCl_2$ and 5.2 grams of triethylamine was charged to a 100 ml. reaction vessel fitted with a gas inlet, stirrer, and a condenser cooled to −78° C. The solution at 15° C. was saturated with $CF_3SO_2F$ gas. Addition of the $CF_3SO_2F$ was achieved by condensation of the gas. The solution was warmed to room temperature and excess $CF_3SO_2F$ gas was removed under reduced pressure. The solution was washed with 30 ml. of 5% HCl, then 30 ml of a saturated NaCl solution. After drying the solution with anhydrous magnesium sulfate, the solvent was removed by distillation to 8–9 torr at 55° C. The yield of the disulfonate ester, a clear, mobile, colorless liquid of formula

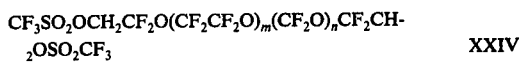

$$CF_3SO_2OCH_2CF_2O(CF_2CF_2O)_m(CF_2O)_nCF_2CH_2OSO_2CF_3 \qquad XXIV$$

was 40.0 grams. The infrared adsorption spectrum showed bands at 6.95 microns characteristic of the sulfonate ester.

EXAMPLE XVII

This example illustrates the preparation of an aromatic amino substituted poly(perfluoroalkylene oxide).

In a dry 250 ml. flask was placed 10 g. (0.006 mole) of the trifluoromethanesulfonate ester (Formula XXIV, $\overline{M}_n = 2200$, $m/n = 0.6$), 2.65 g. of an anhydrous mixture (4:1 molar ratio) of sodium p-nitrophenoxide and p-nitrophenol (containing 0.013 mole of the sodium salt), 125 ml. of redistilled benzotrifluoride, and 5 ml. of dry dimethylsulfoxide. The mixture was stirred magnetically and refluxed for a total of 40 hours and stripped under water aspirator vacuum at about 60° C. The residual amber liquid was dissolved in about 200 ml. of 1,1,2-trichlorotrifluoroethane and the organic solution washed several times with water, dried over anhydrous sodium sulfate, filtered, and concentrated at the aspirator and finally at 0.1 mm Hg pressure on the steam bath. The residual pale yellow oil weighed 6.5 g. Infrared analysis and proton and fluorine nuclear magnetic resonance spectra were consistent for the expected nitrophenoxymethyl derivative; nmr peaks were found at 77.5 and 79.6 $\phi$, 5.56$\tau$, 3.00$\tau$, and 1.81$\tau$.

These properties are consistent with the formula:

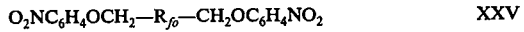

$$O_2NC_6H_4OCH_2-R_{fo}-CH_2OC_6H_4NO_2 \qquad XXV$$

A solution of 8.6 g. of the dinitro compound in 30 ml. trifluoroethanol was hydrogenated in a Parr apparatus in the presence of 0.12 g. platinum oxide. The reaction mixture was subjected to vigorous shaking and about 50 psi hydrogen gas pressure over a 0.5 hr. period at room temperature. After centrifuging to remove catalyst, evaporation of solvent under vacuum gave 8.0 g. of a pale amber oil, which darkened slowly on exposure to air. The equivalent weight of the diamine produce measured as 1090 by titration.

Infrared analysis and nmr resonance absorption at 78.3 and 80.5$\phi$, 5.82$\tau$, 3.30$\tau$, and 3.52$\tau$ are consistent with the structure:

$$H_2NC_6H_4OCH_2-R_{fo}-CH_2OC_6H_4NH_2 \qquad XXVI$$

EXAMPLE XVIII

This example illustrates the preparation of an aliphatic diamino-terminated poly(perfluoroalkylene oxide). Twenty grams of the alpha, omega disulfonate ester perfluoroether polymer of formula XXIV ($\overline{M}_n = 2200$, $m/n = 0.6$) and 5.0 grams of liquid anhydrous ammonia were charged into a glass pressure vessel cooled to 78° C. The pressure vessel was heated at 100° C. for 5 hours, then cooled and opened. The contents, which consisted of 2 layers, were diluted with 50 cc. of $CF_2ClCFCl_2$. The bottom layer was washed with water and dried over anhydrous magnesium sulfate. The solvent was evaporated under reduced pressure, finally bringing the temperature to 100° C. at 1 torr. The product was filtered through sintered glass to remove trace contaminants. 16.4 grams (93.8%) of a slightly yellow clear liquid of formula:

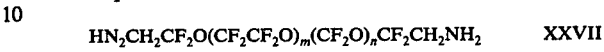

$$HN_2CH_2CF_2O(CF_2CF_2O)_m(CF_2O)_nCF_2CH_2NH_2 \qquad XXVII$$

was obtained. Titration with $CF_3SO_3H$ gave an amine equivalent weight of 1140. The infrared absorption spectrum showed a new band at 2.95 microns for the $NH_2$ group, and the absence of the sulfonate band. Elemental analysis showed sulfur content under 0.001%.

Polyamine copolymers can be prepared, for example, by reaction of a formula XXVI compound with a difunctional alkylating agent such as an alpha-omega disulfonate ester like formula XXIV $CH_3SO_2OCH_2C_6H_4$—O—$C_6H_4CH_2OSO_2CH_3$, or 1,10-decane dibromide.

Polymeric Schiff bases can be prepared by reaction of aliphatic or aromatic dialdehydes or diketones such as phthaloyl dialdehyde or adipaldehyde, free of other amine-reactive groups, with polyether diprimary amines such as Compounds 4 and 31 of Table I. Similarly, such polymers may be prepared by reaction of an aldehyde-terminated poly(perfluoroalkylene oxide), such as Compound 47 of Table I, with diprimary amines, such as Compounds 4 and 31, hexamethylene diamine, or benzidine.

EXAMPLE XIX

This example illustrates the preparation of an acrylate-terminated poly(perfluoroalkylene oxide) and its polymers.

A mixture consisting of 25 g. of a formula XX dicarbinol, 2.9 g. of triethylamine, and 100 ml. of $CCl_2FCF_2Cl$ ("Freon-113") was stirred in a round bottom glass flask and 2.9 g. of purified methacrylyl chloride was added dropwise. There was an immediate exotherm and formation of a white precipitate (triethylamine hydrochloride). Stirring was continued for 6 hours. The resulting mixture was filtered to remove the white solid and the filtrate evaporated to leave 21.2 g. of colorless oil. This was characterized as

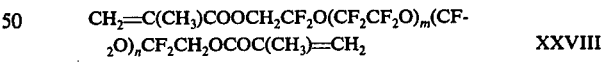

$$CH_2=C(CH_3)COOCH_2CF_2O(CF_2CF_2O)_m(CF_2O)_nCF_2CH_2OCOC(CH_3)=CH_2 \qquad XXVIII$$

by its infrared absorption spectrum which had bands at 5.8 $\mu$ (ester) and 6.2 $\mu$ (double bond). The OH band at 2.9 $\mu$ was absent.

A mixture consisting of 10.0 g. of Compound XXVIII, 40 g. of xylenehexafluoride, 0.1 g. of azobisisobutyronitrile (free radical initiator), and 0.15 g. of octylmercaptan (molecular weight modifier) were placed in a glass bottle. The bottle was purged of air and blanketed under nitrogen, and sealed. It was heated to 65° C. for 16 hrs. while gently shaken. The resulting solution was evaporated to leave a soft clear elastomeric material which showed plastic flow at room temperature. This polymer exhibited a $T_g$ of −125° C.

Other acrylic monomers can be made from hydroxyl-terminated or amino-terminated poly(perfluoroalkylene oxides), such as Compound 3, Table I, or the diamine XXVII, by reaction with an acylic acid halide or anhydride in the presence of a tertiary amine. These monomers can be utilized in the same manner as exemplified above.

These acrylic monomers may be co-polymerized with other monomers, such as alkyl acrylates or methacrylates, to modify the physical properties of the final product. Other acrylic monomers containing reactive functional groups may be incorporated, usually in amounts of 10% by weight or less, into the polymers formed from the poly(perfluoroalkylene oxide) acrylic monomers. For example, glycidyl acrylates, 3-(triethoxysilylpropyl) acrylates, N-methylol acrylamide, and acrylyl halides may be incorporated to improve adhesion to substrates and to provide covalently-bound curing sites, such polymers being curable by heat, acid catalysts or moisture.

EXAMPLE XX

This example illustrates the preparation of a hydroxy-terminated poly(perfluoroalkylene oxide), useful in preparing polyurethane.

Two moles of the methylol-terminated prepolymer of formula XX was reacted with 1 mole of glycidol in the presence of sodium methoxide. The reaction mixture was heated to 90° C. and held at that temperature for 1.5 hrs., after which the mixture was allowed to stand and cool overnight. The reaction mixture was dissolved in "Freon-113". The solution was washed with 10% aqueous sulfuric acid and then washed with saturated aqueous sodium chloride and dried over magnesium sulfate. The dried solution was filtered and concentrated under reduced pressure to yield a yellow liquid hydroxy-terminated prepolymer; it had an equivalent weight of 830 and hydroxyl functionality of 2.4.

EXAMPLE XXI

This example illustrates the preparation of a cyanate-terminated poly(perfluoroalkylene oxide) useful in preparing a polyether-polycyanate.

A 14 g. sample of 4,4'-oxydiphenol was partially neutralized with 1.2 g. of sodium hydroxide in methanol followed by evaporation to dryness under vacuum.

Following the alkylation procedure of Example XVII, the above salt was reacted with 30 g. of the trifluoromethanesulfonate ester-terminated poly(perfluoroalkylene oxide) of formula XXIV. A total of 24.1 g. of the desired $-CH_2OC_6H_4OC_6H_4OH$ terminated poly(perfluoroalkylene oxide) was obtained as a waxy solid. Reaction of this product with excess cyanogen bromide/triethylamine in acetone at $-30°$ C. afforded the corresponding cyanate-terminated poly(perfluoroalkylene oxide). The infrared absorption spectrum shows an absorption peak at 4.4 microns, characteristic of the —OCN group.

EXAMPLE XXII

This example illustrates the preparation of a cyanate-terminated poly(perfluoroalkylene oxide) useful in making a polybenzoxazole-polycyanurate.

Reaction of the hydroxy-terminated poly(perfluoroalkylene oxide) of formula XVI with excess cyanogen bromide/triethylamine in acetone at $-30°$ C. afforded the corresponding cyanate-terminated poly(perfluoroalkylene oxide) having an absorption at 4.4 microns in the infrared absorption spectrum. Heating this material for three weeks at 150° C. resulted in a dark colored rubber, a polybenzoxazole-polycyanurate.

EXAMPLE XXIII

This example illustrates the preparation of a carboxy-terminated poly(perfluoroalkylene oxide), useful in making a polyamide-polyester-polyether.

A suspension of 20 g. of 4-aminobutyric acid in 140 ml. of a methanol solution containing 7 g. of sodium hydroxide was added, with stirring, to a solution of 100 g. of dimethylester-terminated poly(perfluoroalkylene oxide) of formula IX, ($\overline{M}_n = 2100$, $m/n = 6.0$) in 300 ml. 1,1,2-trichlorotrifluoroethane and 100 ml. diethyl ether. The mixture was stirred at room temperature for 2 hrs., and the solvents removed under vacuum. The white powdery residue was acidified with 300 ml. portions of water. The product was given a final wash with 800 ml. acetone and dried under vacuum at 60° C. The liquid product was then dissolved in N/N-dimethylformamide, centrifuged, the solvent removed and again vacuum dried. The yield was 94 g. The acid equivalent weight of the terminated poly(perfluoroalkyleneoxide), terminated with $-CONH(CH_2)_3CO_2H$, was 1210.

EXAMPLE XXIV

This example illustrates the preparation of a functional silane-terminated poly(perfluoroalkylene oxide) useful in making a polyether-polysiloxane.

In a glass ampoule was placed 25 g. (22.4 meq.) of allyl-terminated poly(perfluoroalkylene oxide (Compound 27, Table I, $\overline{M}_n = 2000$, $m/n = 0.6$), 4.4 g. (18.4 meq.) of dimethylactoxysilane, 0.65 g. (4.0 meq.) of methyldiacetoxysilane and 3 drops of a 3% solution of $H(PtCl_3 \cdot C_2H_2)$ in $CCl_4$. The sealed tube was heated at 80° C. for 65 hours. The liquid product, a silane-terminated poly(perfluoroalkylene oxide), $$R_{fc}[-CH_2O(CH_2)_3Si(CH_3)_n(O_2CCH_3)_{3-n}]_2 \qquad \text{XXIX}$$

where $n = 1$ and 2.

Various modifications and alterations of this invention will become apparent to those skilled in the art without departing from the scope and spirit of this invention.

What is claimed is:

1. Linear functionally-terminated poly(perfluoroalkylene oxide) compounds having the formula $$A-CF_2-O-(CF_2CF_2O)_{\overline{m}}(CF_2O)_{\overline{n}}CF_2-A'$$

where A and A' are $-X_aYZ_b$ or $-X'_{a'}Y'Z'_{b'}$, X and X' are each a polyvalent linking organic radical, Y and Y' are each a polyvalent linking organic radical free of non-aromatic double bonds, Z and Z' are each a polymerizable functional group, a and a' are zero or one, b and b' are integers of 1 to 3, m and n designate the number of randomly distributed perfluoroethyleneoxy and perfluoromethyleneoxy subunits, respectively, the ratio m/n being 0.2/1 to 5/1, said compounds having a number average molecular weight of 500 to 20,000, a glass transition temperature lower than $-78°$ C, and polymerizable to polymers having recurrent backbone units of the formula $-CF_2O(CF_2CF_2O)_{\overline{m}}(CF_2O)_n-CF_2-$ which impart to the polymers a glass transition temperature lower than $-78°$ C.

2. Linear hydroxy-terminated poly(perfluoroalkylene oxide) compounds having a number average molecular weight of 500 to 10,000 and the general formula $$R-CF_2-O-(CF_2CF_2O)_m(CF_2O)_nOCF_2-R'$$

where R and R' are hydroxy-substituted organic radicals, where $m$ and $n$ designate randomly distributed perfluoroethyleneoxy and perfluoromethyleneoxy backbone subunits, respectively, the ratio $m/n$ being 0.2/1 to 5/1, said compounds having a glass transition temperature lower than $-78°$ C and polymerizable to polyurethanes having recurrent backbone units of the formula $-CF_2O-(CF_2CF_2O)_m(CF_2O)_n-CF_2-$ which impart to the polyurethanes a glass transition temperature lower than $-78°$ C.

3. The poly(perfluoroalkylene oxides) of claim 2 where R and R' are methylol.

4. The poly(perfluoroalkylene oxides) of claim 2 wherein said ratio $m/n$ is 0.7/1 to 1.6/1, and said glass transition temperature is lower than $-90°$ C.

5. The poly(perfluoroalkylene oxides) of claim 2 having a number average molecular weight of 800 to 5,000.

6. The poly(perfluoroalkylene oxides) of claim 2 wherein R and R' are hydroxy-substituted aliphatic radicals.

7. The poly(perfluoroalkylene oxides) of claim 2 wherein R and R' are devoid of active hydrogen atoms more reactive with isocyanato than said hydroxy substituent and, in addition to said hydroxy substituent, can contain substituents which are non-reactant with isocyanato.

8. The poly(perfluoroalkylene oxides) of claim 2 wherein R and R' have less than 12 carbon atoms and are otherwise unsubstituted or contain other substituents which are non-reactive with isocyanato.

9. Liquid, linear hydroxy-terminated poly(perfluoroalkylene oxides) having a glass transition temperature lower than $-78°$ C., a number average molecular weight of 500 to 10,000, and having the general formula $$HOCH_2-CF_2O-(CF_2CF_2O)_m(CF_2O)_n-CF_2-CH_2OH$$

where $m$ and $n$ designate randomly distributed perfluoroethyleneoxy and perfluoromethyleneoxy backbone subunits, respectively, the ratio $m/n$ being 0.2/1 to 5/1.

10. The poly(perfluoroalkylene oxides) of claim 9, said ratio $m/n$ is 0.7/1, said glass transition temperature is less than $-100°$ C., said poly(perfluoroalkylene oxides) having a number average molecular weight of 1700 to 2840.

11. Liquid, linear hydroxy-terminated poly(perfluoroalkylene oxide) compounds having a glass transition temperature lower than $-78°$ C, a number average molecular weight of 500 to 10,000, and having the general formula $$R-CF_2O-(CF_2CF_2O)_m(CF_2O)_n-CF_2-R'$$

where R and R' are hydroxy-substituted aliphatic radicals, where $m$ and $n$ designate randomly distributed perfluoroethyleneoxy and perfluoromethyleneoxy backbone subunits, respectively, the ratio $m/n$ being 0.2/1 to 5/1, said compounds being polymerizable to polyurethanes having recurrent backbone units of the formula $-CF_2O-(CF_2CF_2O)_m(CF_2O)_n-CF_2-$ which impart to the polyurethanes a glass transition temperature lower than $-78°$ C.

* * * * *